United States Patent
Peesapati et al.

(10) Patent No.: US 10,987,458 B2
(45) Date of Patent: Apr. 27, 2021

(54) METHOD OF USING A MEDICAL FLUID GENERATING MACHINE

(71) Applicant: Fresenius Medical Care Holdings, Inc., Waltham, MA (US)

(72) Inventors: Sameer Peesapati, Pittsburg, CA (US); Martin Joseph Crnkovich, Walnut Creek, CA (US); David Yuds, Hudson, NH (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 123 days.

(21) Appl. No.: 16/229,134

(22) Filed: Dec. 21, 2018

(65) Prior Publication Data
US 2020/0197589 A1 Jun. 25, 2020

(51) Int. Cl.
*A61M 1/16* (2006.01)
*G16H 20/17* (2018.01)

(52) U.S. Cl.
CPC .......... *A61M 1/1656* (2013.01); *A61M 1/168* (2013.01); *G16H 20/17* (2018.01); *A61M 2205/6072* (2013.01)

(58) Field of Classification Search
None
See application file for complete search history.

(56) References Cited

U.S. PATENT DOCUMENTS

| 4,199,050 A | * | 4/1980 | Moller | B65B 21/20 198/429 |
| 4,668,400 A | * | 5/1987 | Veech | A61M 1/1656 210/647 |
| 5,000,345 A | * | 3/1991 | Brogna | B67D 1/00 141/103 |

(Continued)

FOREIGN PATENT DOCUMENTS

| EP | 2011529 | 1/2009 |
| EP | 2035059 | 3/2009 |

(Continued)

OTHER PUBLICATIONS

TRUTOL(TM) spec sheet, https://www.thermofisher.com/document-connect/document-connect.html?url=https%3A%2F%2Fassets.thermofisher.com%2FTFS-Assets%2FCDD%2FPackage-Inserts%2FJL840906-Trutol-Glucose-Tolerance-Beverages.pdf&title=VHJ1dG9sIEdsdWNvc2UgVG9sZXJhbmNIIEJldmVyYWdlcyBQYWNrYWdlIEluc2VydCBIDRU5d (Year: 2020).*

(Continued)

*Primary Examiner* — Chester T Barry
(74) *Attorney, Agent, or Firm* — Fish & Richardson P.C.

(57) ABSTRACT

A method of preparing a medical fluid with a medical fluid generating machine includes receiving, at the medical fluid generating machine, a container to be filled with the medical fluid, receiving, at a processor, instructions to prepare the medical fluid, the instructions including an identification a medical fluid type from among a plurality of medical fluids and a desired volume of the medical fluid, preparing the (Continued)

medical fluid according to the received instructions, testing the prepared medical fluid to ensure that one or more characteristics of the prepared medical fluid is within an acceptable range, filling the container with the prepared fluid and labelling the container with information about the medical fluid, the information including the identification of the medical fluid type within the filled container, and an expiration date of the fluid.

22 Claims, 11 Drawing Sheets

(56) References Cited

U.S. PATENT DOCUMENTS

| | | | |
|---|---|---|---|
| 5,605,627 A | 2/1997 | Carlsen et al. | |
| 6,146,536 A * | 11/2000 | Twardowski | A61M 1/3647 210/646 |
| 7,300,636 B2 | 11/2007 | Taylor | |
| 7,387,734 B2 | 6/2008 | Felding | |
| 9,090,449 B2 * | 7/2015 | Crisp, III | B67D 1/0022 |
| 9,117,326 B2 * | 8/2015 | Cerveny | B65B 43/123 |
| 9,198,830 B2 | 12/2015 | Kugelmann et al. | |
| 9,550,662 B1 * | 1/2017 | Brown | B67D 7/24 |
| 9,865,023 B2 * | 1/2018 | Insolia | G06Q 50/04 |
| 10,043,226 B2 * | 8/2018 | Craparo | G06Q 50/12 |
| 10,125,002 B2 * | 11/2018 | Volftsun | G01F 11/06 |
| 2014/0276373 A1 | 9/2014 | Minkus | |
| 2017/0049858 A1 * | 2/2017 | Prestrelski | A61K 38/1816 |
| 2017/0116662 A1 * | 4/2017 | Ranganath | G06Q 30/0635 |
| 2017/0266227 A1 * | 9/2017 | Almas | A61K 33/20 |
| 2020/0230197 A1 * | 7/2020 | Phillips | A23L 33/155 |

FOREIGN PATENT DOCUMENTS

| | | |
|---|---|---|
| EP | 2841125 | 3/2015 |
| GB | 2064938 A1 * | 6/1981 |
| WO | WO 2007/144427 | 12/2007 |
| WO | WO 2013/159883 | 10/2013 |

OTHER PUBLICATIONS

Scheffers Medical Drain Line Anchor, Model H Instructions, 2018, 4 pages.
Scheffers Medical Drain Line Anchor, Model S Instructions, 2018, 4 pages.
Scheffers Medical Drain Line Anchor, Model H Brochure, 2018, 2 pages.
PCT International Search Report and Written Opinion in Application No. PCT/US2019/063560, dated Jun. 29, 2020, 13 pages.

* cited by examiner

METHOD OF USING A MEDICAL FLUID GENERATING MACHINE

TECHNICAL FIELD

This invention relates to generating medical fluid and using reusable medical fluid bags.

BACKGROUND

Saline is a solution of purified, sterile water containing 0.9% sodium chloride (NaCl). Saline-like solutions are useful for a variety of self and home-care solutions ranging from simple oral, eye, and nasal care to dialysis at home. The operational costs associated with manufacturing saline are typically passed on to healthcare providers and home care patients.

Hemodialysis treatments typically require a minimum of two one-liter bags of saline, used for priming the bloodlines at the beginning of the treatment and flushing the blood back to the patient at the end of treatment. An average hemodialysis clinic uses an average of 21,000 bags of saline a year. Saline bags and other fluids for IV infusion of patients, such as for peritoneal dialysis, generate many waste bags and at the same time offer a large amount of overhead effort due to inventory management, storage, and tracking of orders. Furthermore, such medical fluids are costly to transport and store, and have a limited shelf life. Clinical settings, hospice care, and patients who use medical fluids such as saline at home generally need saline delivered, stored, and expiration tracked. The ergonomics of lifting several cases of fluid may lead to back and spine injuries. The magnitude of possible expenses is magnified in a home or hospice setting.

SUMMARY

Fluid for infusion is currently produced online for some therapeutic machines. For example, certain dialysis machines include the ability to generate dialysate for a dialysis treatment within the machine for use in that machine's current treatment at certain times. However, this fluid is typically not stored or distributed to other dialysis machines or used outside of the times during which the machine is delivering dialysis therapy. By providing a machine for the clinic that is dedicated to the production of substitution fluid or saline for use in multiple different dialysis machines, the clinic will immediately realize cost-savings. The systems described herein could also be used in any medical environment, from hospitals to disaster response units to developing countries, where saline is difficult to obtain and even potable water is scarce. These fluid generation and filling stations can be located in pharmacies, clinics, disaster units, military camps, medical camps, all types of healthcare facilities, and can be incorporated into systems for safety for manufacturing, mining, and any facility where human injury is a possible concern.

In some embodiments, a method of preparing a medical fluid with a medical fluid generating machine includes receiving, at the medical fluid generating machine, a container to be filled with the medical fluid, receiving, at a processor, instructions to prepare the medical fluid, the instructions including an identification a medical fluid type from among a plurality of medical fluids and a desired volume of the medical fluid, preparing the medical fluid according to the received instructions, testing the prepared medical fluid to ensure that one or more characteristics of the prepared medical fluid is within an acceptable range, filling the container with the prepared fluid; and labelling the container with information about the medical fluid, the information including the identification of the medical fluid type within the filled container, and an expiration date of the medical fluid.

Implementations of the method can include one or more of the following features. Preparing the medical fluid comprises automatically determining if the medical fluid is to be gravimetrically, volumetrically, or conductivity-proportioned. Preparing the medical fluid comprises selecting one or more solutes from a plurality of available solute sources to prepare the medical fluid based on the identification of medical fluid type, measuring a required amount of the one or more solutes based on the desired volume, delivering the measured amounts of the one or more solutes to a reservoir within the machine, and mixing the delivered amounts of one or more solutes with a volume of water, the volume of water determined by the desired volume. Preparing the medical fluid comprises selecting one or more solutes from a plurality of solute sources to prepare the medical fluid based on the identification of the medical fluid type and displaying an alert if one or more of the selected solute sources is not available to the machine. Displaying an alert that the prepared medical fluid is defective upon detecting that the one or more characteristics of the prepared fluid is not within the acceptable range. Sterilizing the container prior to filling the container with fluid. Sterilizing the container comprises filling the container with disinfectant and emptying the disinfectant from the container. Sterilizing comprises irradiating the container with UV radiation. Labelling the container comprises affixing a label to an outside of the container. Labelling the container comprises sending instructions to a screen affixed to the container to display the information about the medical fluid. Sealing a side of the filled container to maintain sterility of the medical fluid within the filled container. Sealing a side of the filled container comprises hermetically sealing a flexible bag of the container which is affixed within a rigid shell of the container. The flexible bag is releasably secured to the rigid shell. The medical fluid is saline. The medical fluid is dialysate. The machine includes a door that opens to uncover a cavity that receives the container. The machine is programmed to make a variety of different medical fluids by being configured for connecting different concentrates to the machine and allowing a user to select any one of multiple different displayed medical fluids.

In some embodiments, a medical fluid generating machine includes a cavity configured to receive a container to be filled with the medical fluid; a processor including instructions for preparing the medical fluid, the instructions including an identification a medical fluid type from among a plurality of medical fluids and a desired volume of the medical fluid; sensors configured to test the prepared medical fluid to ensure that one or more characteristics of the prepared medical fluid is within an acceptable range; a fluid line connected to the container for filling the container with the prepared fluid; and a labelling device configured to label the container with information about the medical fluid, the information including the identification of the medical fluid type within the filled container, and an expiration date of the medical fluid.

In some embodiments, a method includes receiving, at a medical fluid generating machine, a container to be filled with a saline substitute, receiving, at a processor, instructions to prepare the saline substitute; preparing the saline substitute in response to the instructions by (a) combining water with and acid concentration and a bicarbonate concentration to form a solution and (b) filtering the solution through one or more filters to achieve a purity of no more than 10-6 CFU/ml and no more than 0.5 EU/ml; testing the prepared saline substitute to ensure that one or more characteristics of the prepared saline substitute is within an acceptable range; filling the container with the tested saline substitute; and labelling the container with information that identifies the saline substitute and provides an expiration date of the saline substitute.

Implementations of the method can include one or more of the following features. Preparing the saline substitute further comprises heating and degassing the solution. Priming a dialysis machine by flowing the prepared saline substitute into the blood line of the dialysis machine prior to a dialysis treatment. Comprising performing the dialysis treatment on a patient. Comprising flushing blood from the blood line back to the patient by pushing the prepared saline substitute into the blood line.

In some embodiments, a medical fluid generating machine includes an outlet configured to fill a removable container with a saline substitute; one or more filters; and a processor configured to receive instructions from a user of the machine for preparing the medical fluid, wherein, responsive to the instructions, the processor is configured to cause the machine to mix water with an acid concentration and a bicarbonate concentration to form a solution, prepare the saline substitute by filtering the solution through the one or more filters to achieve a purity of no more than 10-6 CFU/ml and no more than 0.5 EU/ml, test the saline substitute to ensure that one or more characteristics of the saline substitute is within an acceptable range, fill the container with the saline substitute via the outlet, and create a label that that identifies the saline substitute and provides an expiration date of the saline substitute.

The saline preparation and filling mechanisms described herein advantageously add value to the medical system by balancing resource utilization (e.g. distribution of infusing fluids), recyclability, and re-usability. The methods and systems described herein advantageously address the shortage of saline, simplify the saline production process, and remove the complication of transfer of saline bags or containers to consumers.

In some embodiments, a method of preparing a medical fluid with a medical fluid generating machine includes receiving, at the medical fluid generating machine, a container to be filled with the medical fluid, receiving, at a processor, instructions to prepare the medical fluid, the instructions including an identification of the medical fluid as saline substitute and a desired volume of the saline substitute, preparing the medical fluid according to the received instructions, filtering the medical fluid through one or more filters, testing the prepared medical fluid to ensure that one or more characteristics of the prepared medical fluid is within an acceptable range, filling the container with the tested medical fluid, and labelling the container with information about the medical fluid, the information including the identification of the medical fluid within the filled container as saline substitute, and an expiration date of the fluid.

In some embodiments, a method of preparing medical fluid includes entering instructions into a fluid preparing machine to prepare a desired volume of a specified medical fluid, connecting a reusable fluid container to the machine to be filled with the medical fluid that is prepared according to the entered instructions, removing the filled reusable fluid container from the machine, and connecting the filled fluid container to a medical machine that uses the fluid in the fluid container. In some implementations, entering instructions includes selecting from a menu of possible medical fluids to be prepared.

In some embodiments, a container configured to contain a medical fluid includes a flexible bag configured to expand when filled with a medical fluid, a rigid exterior shell bonded to the flexible bag, the rigid exterior shell configured to contain and support the flexible bag within the rigid exterior shell when the flexible bag is filled with the medical fluid. The rigid exterior shell includes a handle at a lateral side of the shell, the handle configured to be grasped by a user, and a hook at a top portion of the shell, the hook configured to suspend the rigid shell and its contents, a fluid inlet at the top portion of the shell, a fluid outlet at a bottom portion of the shell, and a valve within the fluid outlet, wherein the container is sterilizable and reusable.

In some implementations, the valve is configured to toggle between blocking and permitting fluid flow through the valve by pressing a clip. The fluid outlet includes a luer connection. A valve is within the fluid inlet that is configured to toggle between blocking and permitting fluid flow through the valve by pressing a clip.

In some embodiments, a method of preparing a medical fluid with a medical fluid generating machine includes receiving, at the medical fluid generating machine, a container to be filled with the medical fluid, receiving, at a processor, instructions to prepare the medical fluid, the instructions including an identification a medical fluid type from among a plurality of medical fluids and a desired volume of the medical fluid, preparing the medical fluid according to the received instructions, testing the prepared medical fluid to ensure that one or more characteristics of the prepared medical fluid is within an acceptable range, filling the container with the prepared fluid and labelling the container with information about the medical fluid, the information including the identification of the medical fluid type within the filled container, and an expiration date of the fluid.

Implementations of the method can include one or more of the following features. Preparing the medical fluid includes automatically determining if the medical fluid is to be gravimetrically, volumetrically, or conductivity-proportioned. Preparing the medical fluid includes selecting one or more solutes from a plurality of available solute sources to prepare the medical fluid based on the identification of medical fluid type, measuring a required amount of the one or more solutes based on the desired volume, delivering the measured amounts of the one or more solutes to a reservoir within the machine, and mixing the delivered amounts of one or more solutes with a volume of water, the volume of water determined by the desired volume. Preparing the medical fluid includes selecting one or more solutes from a plurality of solute sources to prepare the medical fluid based on the identification of the medical fluid type and displaying an alert if one or more of the selected solute sources is not available to the machine. Displaying an alert that the prepared medical fluid is defective upon detecting that the one or more characteristics of the prepared fluid is not within the acceptable range. Sterilizing the container prior to filling the container with fluid. Sterilizing the container includes filling the container with disinfectant and emptying the disinfectant from the container. Sterilizing includes irradiating the container with UV radiation. Labelling the container includes affixing a label to an outside of the container. Labelling the container includes sending instructions to a screen affixed to the container to display the information about the medical fluid. Sealing a side of the filled container to maintain sterility of the medical fluid within the filled container. Sealing a side of the filled container includes hermetically sealing a flexible bag of the container, which is affixed within a rigid shell of the container. The flexible bag is releasably secured to the rigid shell. The medical fluid is saline. The medical fluid is dialysate. The machine includes a door that opens to uncover a cavity that receives the container. The machine is programmed to make a variety of different medical fluids by being configured for connecting different concentrates to the machine and allowing a user to select any one of multiple different displayed medical fluids.

In some embodiments, a medical fluid generating machine includes a cavity configured to receive a container to be filled with the medical fluid, a processor including instructions for preparing the medical fluid, the instructions including an identification a medical fluid type from among a plurality of medical fluids and a desired volume of the medical fluid, sensors configured to test the prepared medical fluid to ensure that one or more characteristics of the prepared medical fluid is within an acceptable range, a fluid line connected to the container for filling the container with the prepared fluid, and a labelling device configured to label the container with information about the medical fluid, the information including the identification of the medical fluid type within the filled container, and an expiration date of the medical fluid.

Advantages of the methods and systems described herein include moving production of saline to hospitals, outpatient settings like clinics, and homes, which reduces the cost of saline used for hemodialysis treatments and other medical treatments. As described, dialysate and other solutions can be set up and provided easily and universally via distributed generation and filling stations.

The details of one or more embodiments of the invention are set forth in the accompanying drawings and the description below. Other features and advantages will be apparent from the description and drawings, and from the claims.

DETAILED DESCRIPTION

Figure 1:
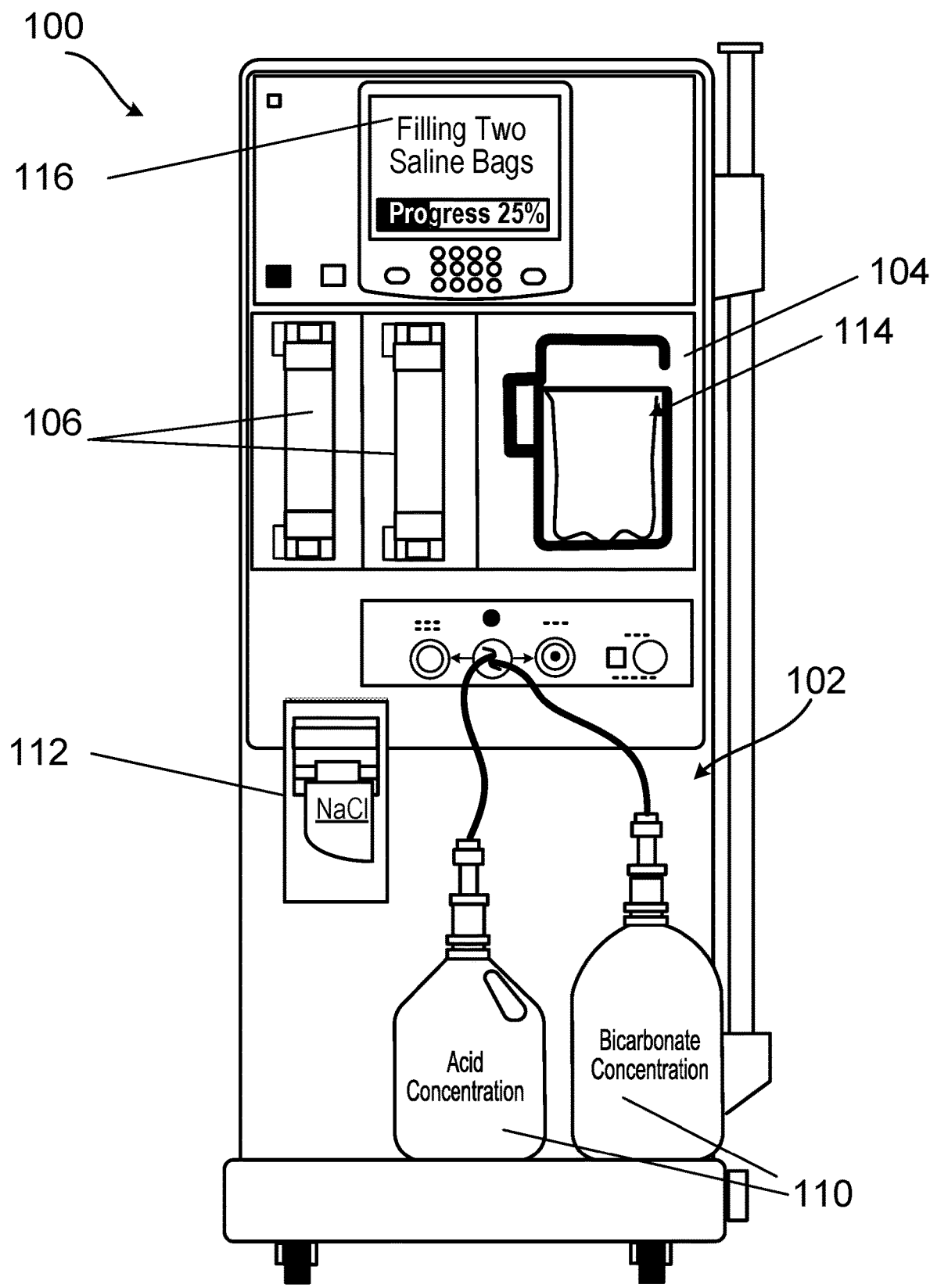
FIG. 1 is a schematic of a medical fluid generating machine with a reusable bag.

FIG. 1 shows a medical fluid generating system 100 with a fluid generation machine 102 that custom generates medical fluid and then fills a reusable fluid container 104 with the generated medical fluid. The fluid generation machine 102 mixes water from a water source with solutes available to the machine from liquid solute sources 110 and/or from solid solute sources 112. The fluid generation machine 102 includes two or more filters 106 that filter water/solute solution. The filters 10 can be, for example, polysulfone filters, such as DIASAFE® filters, available from Fresenius, Waltham Mass. and/or dialyzers. This filtration results in a medical fluid that has $10^{-6}$ CFU/ml (colony-forming units per milliliter) or less and 0.5 EU/ml (endotoxin units per milliliter) or less, which makes the fluid suitable for infusion or other suitable medical use. Although the illustrated example utilizes two polysulfone filters to achieve the aforementioned purity, it should be understood that any suitable number (including a single filter) and types of filters may be used in other examples, so long as the resulting fluid is suitably pure (in this case, meeting the $10^{-6}$ CFU/ml and 0.5 EU/ml thresholds). Once the customized medical fluid 114 is prepared and tested for quality, the fluid generation machine 102 fills the reusable fluid container 104 with the newly made customized medical fluid 114.

In some examples, the water used by the fluid generation machine 102 is purified water from a centralized water purification system, such as a reverse osmosis (RO) water purification and distribution systems implemented in many dialysis clinics. In some examples, the fluid generation machine 102 itself includes a water purification module (e.g., a reverse osmosis purification module).

In some examples, the fluid generation machine 102 can fill bags for custom substitution fluid for hemodiafiltration (HDF) treatments in existing hemodialysis machines. With the fluid generating system 100, a clinic may eliminate the need to purchase costly HDF machines that require ultrafiltrate as added fluid during the course of a standard treatment. Instead, using the fluid generating system 100, the clinic could fill a sterile container (either a single use or a re-usable fluid container) with normal saline mixed with other key constituents in controlled proportions on-site, and infuse the fluid into a patient during a hemodialysis treatment. Additionally, the fluid generating system 100 could be configured to include other constituents like dextrose and lactate to locally fill peritoneal dialysis (PD) solution bags.

The fluid generation machine 102 is generally located on-site at a clinic, hospital, or home that uses dialysate, saline, or other medical fluid. By making the fluid generation machine 102 portable and multifunctional in that it can produce one or more medical fluids, medical fluid users can produce a needed fluid on-site, eliminating the need to transport and store that medical fluid (e.g., saline, dialysate, etc.). The reusable fluid container 104 can be used to provide saline, IV, HD infusate, HDF infusate, peritoneal dialysate, and other solutions to address various medical purposes for life support, self-care, and home care needs.

To generate a customized medical fluid 114, a user (such as a clinician or a patient) interacts with a display or user interface 116 to choose a desired medical fluid from a menu of possible medical fluids that can be generated by the fluid generating system 100. The user interface 116 includes buttons that the user can select to make elections about the desired output, such as the type and quantity of a customized medical fluid 114. In addition to the type of medical fluid and the volume of fluid to be generated, these selections can include the number of containers to be filled, among other fluid output details.

Once programmed and instructed by the user, the fluid generating system 100 draws in liquid solutes such as acid concentrate and bicarbonate as inputs from liquid solute sources 110 to mix with purified water and create dialysate. The fluid generation machine alternatively or additionally can draw in solid solutes such as sodium chloride from solid solute sources 112 to mix with water to create saline. The liquid solute sources 110 and solid solute sources 112 can be containers or pods attached to the fluid generation machine 102. As most medical fluids require water, the fluid generation machine 102 also draws in reverse-osmosis (e.g., purified) water, and proportions, heats and degasses, tests, and ultrafilters the resulting solution as needed to produce a final customized medical fluid that it supplies to one or more reusable fluid containers 104. As indicated above, in some instances, the fluid generating system 100 can include equipment for reverse-osmosis or other method of water purification. The purification equipment can be located within a separate machine, or located within the body of the fluid generation machine 102.

Generally, the user inputs parameters that define a desired a customized solution batch by selecting from a menu of preset choices. The preset choices can include a variety of medical fluids, (e.g., saline, dialysate, etc.), a volume of fluid to be generated, and number of containers to be generated. In some instances, the fluid generating system 100 detects if the correct liquid solute sources 110 and/or solid solute sources 112 are attached to the fluid generation machine to carry out the selected fluid generation request. The fluid generating system can also determine if sufficient amounts of liquid solutes and/or solid solutes remain within liquid solute sources 110 and solid solute sources 112, such as by gravimetric testing of the liquid solute sources 110 and solid solute sources 112. The fluid generating system 100 makes the selected solution, automatically determining whether to use volumetric, gravimetric, refractometric or conductivity-based measurements based on the raw materials required for the solution (e.g., if solid or liquid solutes are required to prepare the requested fluid). Once mixed, the quality of the resulting prepared solution is tested in the cartridge or mixing chamber in which the solution is mixed inside the fluid generating system 100. The fluid generation machine 102 dispenses the prepared and tested solution into waiting reusable fluid container(s) 104. In some instances, before dispensing the fluid into the reusable fluid container(s) 104, the fluid generation machine 102 performs a check to identify the attached reusable fluid container(s).

Figure 2A:
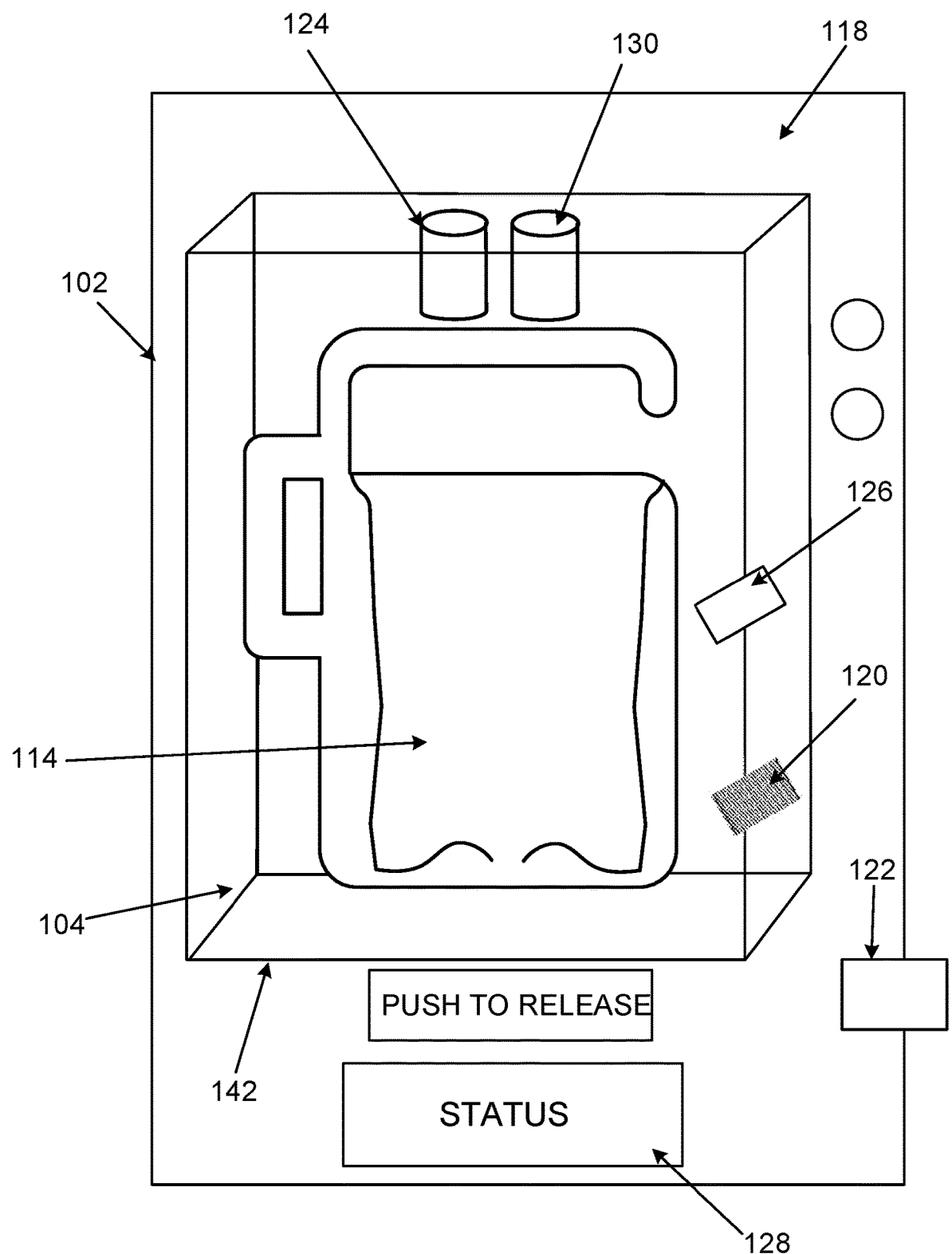
FIGS. 2A-C are close up views of a portion of the medical fluid generating machine of FIG. 1.

FIG. 2A shows a close up front view of a portion of the fluid generation machine 102 where a reusable fluid container 104 is attached. To use the fluid generating system 100, a user first attaches a reusable container 104 to the fluid generation machine 102 at this container attachment site 118. In some instances, the user must open (e.g., slide or swing open) a door 142 before the reusable container 104 can be attached to the fluid generation machine 102 at the container attachment site 118. For safety, the fluid generating system 100 identifies the reusable fluid container 104 via a unique identifier 120 attached to the reusable fluid container 104. For example, the fluid generation machine 102 uses a scanner 122 to scan the unique identifier 120 (such as a bar code) that is printed or engraved on the reusable fluid container 104. The fluid generating system 100 can look up information related to the unique identifier 120 to identify the specific reusable fluid container 104 attached to the machine and associated information. For example, if the fluid generating system 100 determines that the identified reusable fluid container 104 attached at the container attachment site 118 has been used more than a recommended number of times, or is older than a given shelf life, the fluid generating system 100 may generate an alarm on the user interface 116 (in FIG. 1). If the scanner 122 detects that a container other than a reusable fluid container 104 has been attached, the fluid generating system 100 may generate an alarm on the user interface 116. Alternatively, a separate status bar 128 may be included.

Once the attached reusable fluid container 104 is deemed acceptable, the fluid generating system 100 then disinfects the reusable fluid container 104 using a sterilizing apparatus 124. The sterilizing apparatus 124 is a source of disinfecting fluid (at either room temperature or elevated temperature) that flushes the reusable fluid container 104. The sterilizing apparatus 124 can also bathe the exterior of the reusable fluid container 104. To ensure that the reusable fluid container 104 is securely attached to the fluid generation machine 102, the fluid generation machine 102 does a leak test to ensure there are no leaks. For example, the fluid generation machine 102 may carry out a pressure-holding test on the reusable fluid container 104. In some embodiments, the sterilizing apparatus is a source of UV radiation for UV sterilization of the reusable fluid container.

Either before, after, and while the reusable fluid container 104 is being sterilized, the user selects the desired customized medical fluid 114 to be generated. The fluid generation machine 102 generates the customized medical fluid 114, and performs a quality check on the generated fluid before dispensing it to the reusable fluid container(s) 104. The fluid generation machine 102 then labels each filled reusable fluid container 104 with a fluid label 126. The fluid label 126 shows information about the contents of the filled reusable fluid container 104, for example, a batch creation date and an expiration date. The fluid label 126 may show that the contents of the container 104 is saline substitute (e.g., medical fluid composed as dialysate and then filtered through filters 106 and suitable for use in the place of saline). The fluid label 126 may be a physical sticker, or may be an update to a screen on the side of the reusable fluid container 104, e.g., an LCD display that is automatically updated with information such as the expiration date. The fluid label 126 may take the form of a bar code, QVC code, NFC or RFID chip. In some implementations, a therapeutic machine (such as a dialysis machine) can read the fluid label 126 and determine if the contents of the reusable fluid container 104 are of the correct variety for use with a therapeutic treatment, and whether the contents are expired. By use of the fluid labels 126, the fluid generating system 100 could be used to monitor both the life of the reusable fluid container 104 by virtue of the unique identifier 120, and the shelf life of the saline itself for inventory purposes by virtue of the fluid label 126.

Figure 2B:
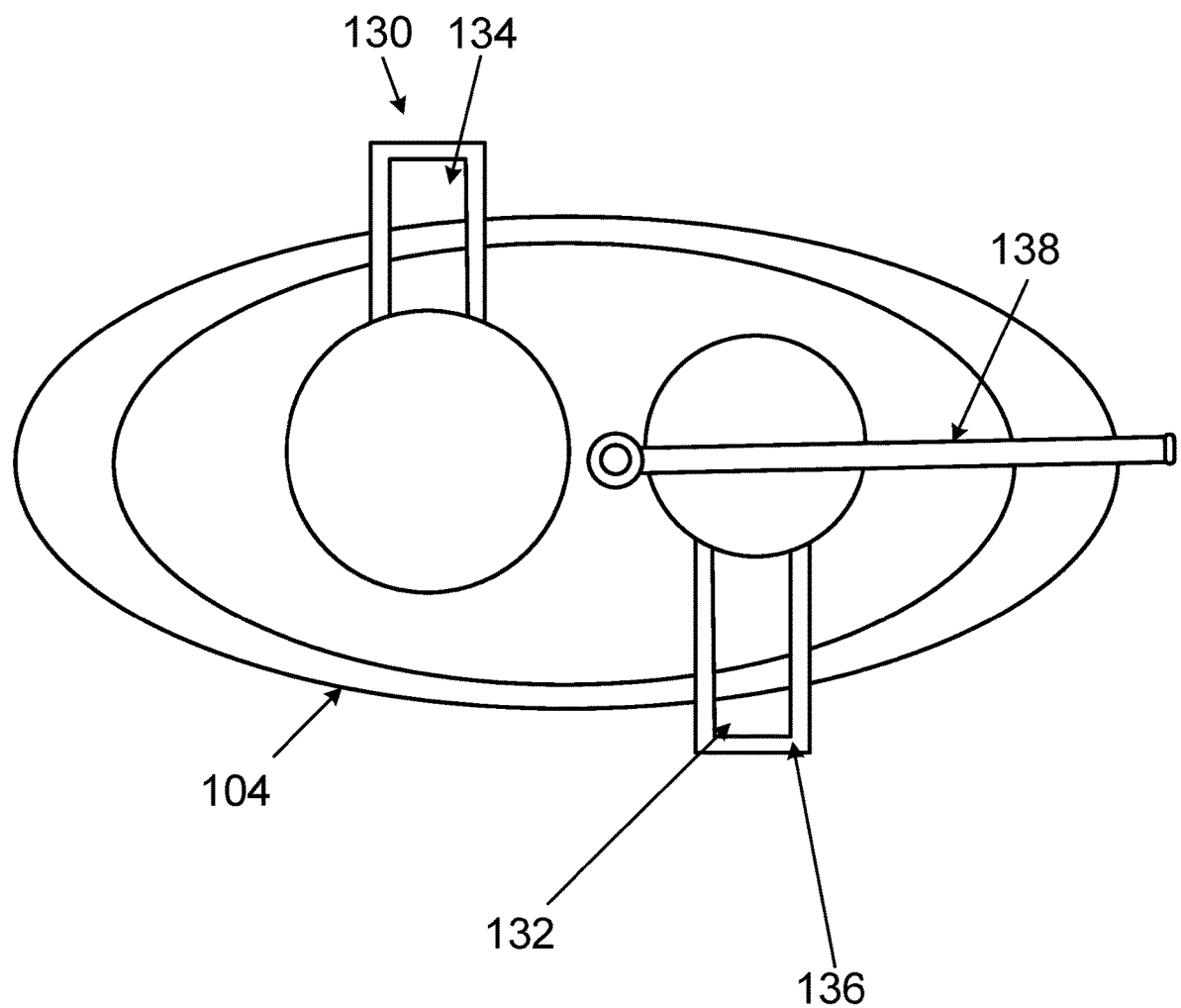

FIG. 2B shows a top view of a portion of the fluid generation machine 102 where a reusable fluid container 104 is attached, e.g., a view of the interface between the machine and the fluid container 104. In one embodiment, a first and second magnetic tip 130, 132 is attached to the fluid generation machine 102 at a saline inlet 134 and disinfectant inlet 136. The magnetic tip 130, 132 can snap into place with a top portion of a reusable fluid container 104 when the top of the reusable fluid container is brought into proximity with either magnetic tip 130, 132. To move the reusable fluid container 104, the reusable fluid container 104 can be connected to a movement device such as rod 138. The rod 138 can spin, translate, rotate, or otherwise move the reusable fluid container 104 so that the top of the reusable fluid container 104 comes into contact with the magnetic tip 130 or magnetic tip 132 and thus the saline inlet 134 and disinfectant inlet 136, respectively.

Figure 2C:
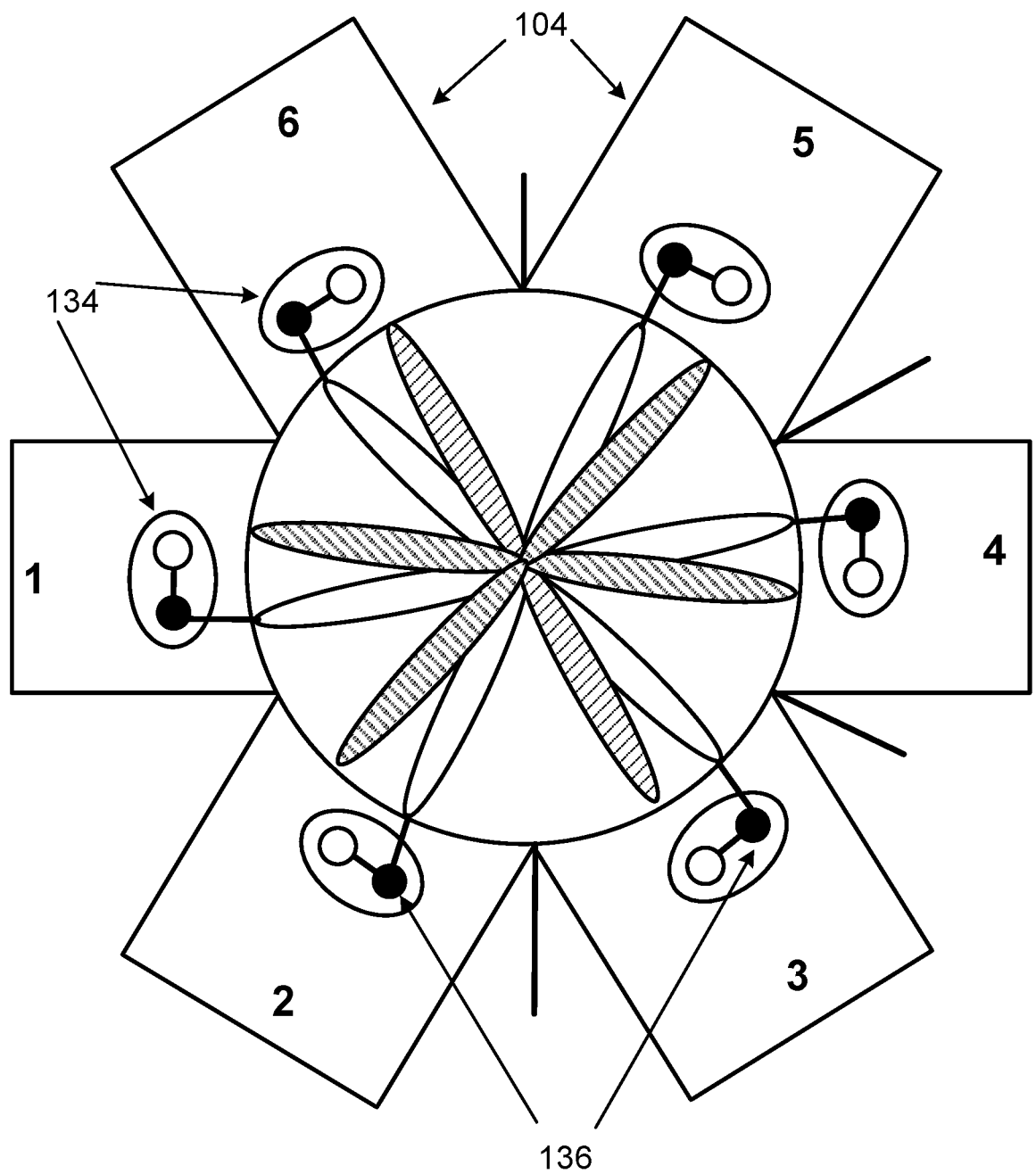

FIG. 2C shows a top view of an implementation of a portion of the fluid generation machine 102 where multiple reusable fluid containers 104 are attached. A carousel 140 attaches multiple reusable fluid containers 104 to the fluid generation machine 102. Each reusable fluid container 104 has a saline inlet 134 and disinfectant inlet 136, allowing multiple reusable fluid containers 104 to be filled simultaneously. Each reusable fluid container 104 is connected to a rod 138 that can spin, translate, rotate, or otherwise move the reusable fluid container 104 so that the top of the reusable fluid container 104 comes into contact the respective saline inlet 134 and disinfectant inlet 136, as needed. In some implementations, the carousel 140 rotates to allow a user to access each of the reusable fluid containers 104 in turn. For example, the carousel 140 and attached reusable fluid containers 104 may all be located within a body of the fluid generation machine 102, and accessible by a single door (e.g., door 142 on FIG. 2A). The user may press a button, or the machine may be configured to rotate automatically and present sequential reusable fluid containers to the door 142 so that the user can attach or remove the containers from the attachment site 118. Sequential access and a blocking door 142 may enclose any fluid (e.g., disinfectant fluid bathing an exterior of the reusable fluid containers 104) and enhance sterility.

Figure 3:
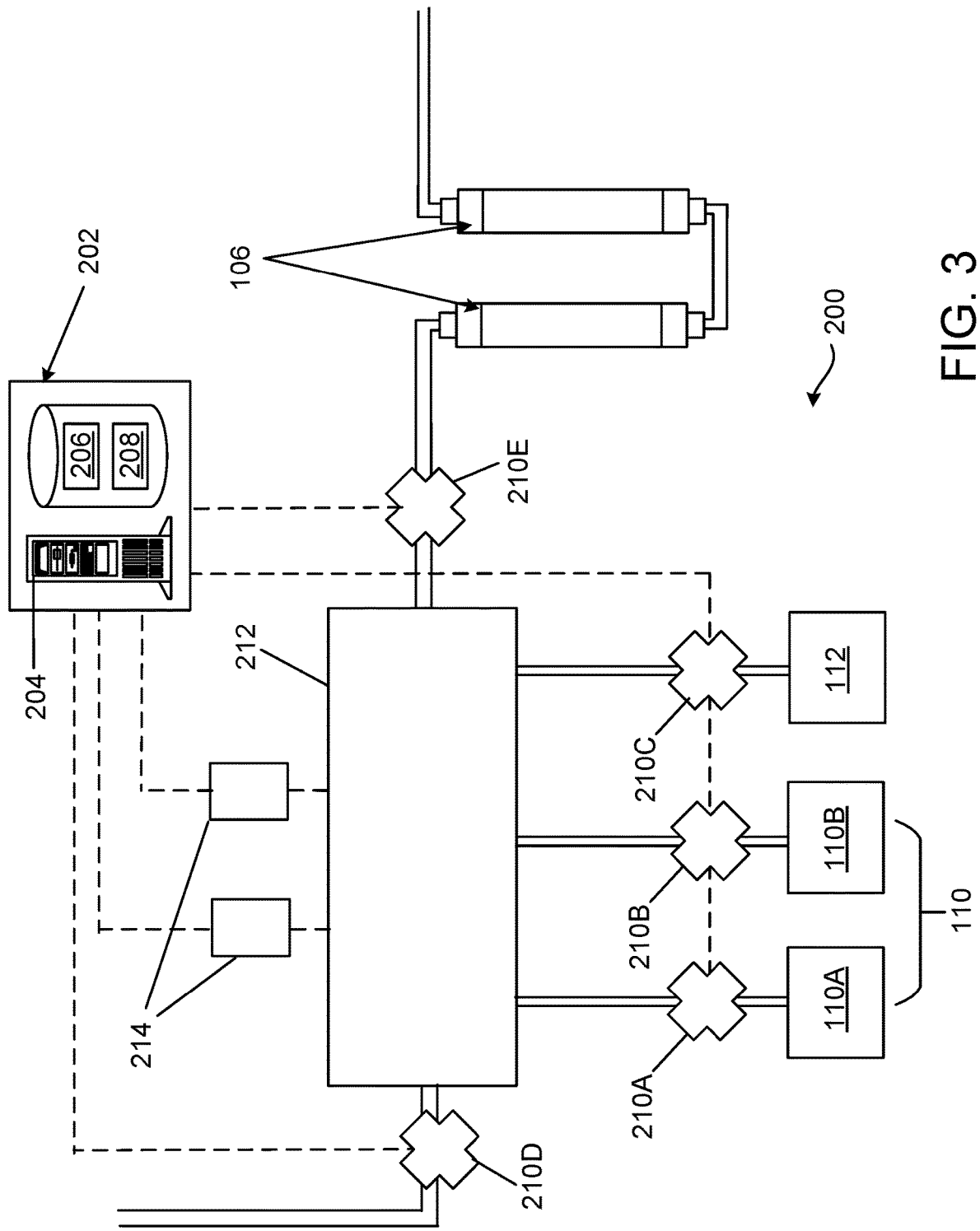
FIG. 3 is a schematic of a hydraulic system of the medical fluid generating machine of FIG. 1.

Referring to FIG. 3, the hydraulic system 200 of the fluid generation machine 102 is controlled by a control unit 202. The control unit 202 includes a processor 204, and a database or memory 206. The memory 206 saves data such as the usage history of the fluid generation machine 102 including the type and quantity of fluids generated over time. Fluid generation profiles 208 can be stored on the memory 206, and are associated with the differing customized medical fluids 114. For example, a specific fluid generation profile 208 can be selected and loaded when the user selects saline. The processor 204 of the control unit 202 interfaces with the memory 206 and the stored fluid generation profiles 208.

The control unit 202 transmits and receives signals from the various components of the hydraulic system 200, including fluid controllers 210. The fluid controllers 210 control the passage of constituents through the hydraulic system 200, including the passage of raw ingredients and the finished solution. For example, fluid controllers 210A and 210B control the speed and volume of liquid solutes that are pumped from liquid solute sources 110A and 110B and delivered to a mixing chamber 212. Fluid controller 210C controls the amount of solid withdrawn from a solute source 112 and delivered to the mixing chamber 212. The fluid controller 210D controls the passage of purified water that is delivered to the mixing chamber 212 and the fluid controller 210E controls the prepared customized medical fluid 114 that exits the mixing chamber 212.

The control unit 202 also transmits signals to and receives signals from sensors 214 that characterize the fluid inside the mixing chamber 212. The sensors 214 can include conductivity sensors, volumetric sensors, scales, pH detectors, thermometers, etc.

The fluid controllers 210 include various fluid control instruments as is known in the art. For example, each fluid controller 210 can include a pump that moves a fluid along an associated fluid line, and a valve that permits or inhibits fluid flow along the associated fluid line. Each fluid controller 210 can also include a fluid flow sensor that detects the volume of fluid flowing through the associated fluid line. The fluid controller 210C can include solid solute control instruments as is known in the art. For example, the fluid controller 210C can include a scale that weighs an amount of solute to be delivered to the mixing chamber 212. The fluid controller 210C can also include fluid flow control instruments, for example a pump that delivers clean water into the solid solute source 112 to dissolve the solid therein and then reverses direction to remove the dissolved solute from the solid solute source 112 container. The fluid controller 210E can include a flow sensor and a conductivity sensor to determine the quantity and salt content of prepared customized medical fluid 114 being dispensed.

The fluid controller 210E can direct the flow of the prepared customized medical fluid 114 through the filters 106. Once filtered through the filters 106, the customized medical fluid can be suitable for use as saline substitute. After the prepared customized medical fluid 114 leaves the mixing chamber 212 it can also pass through elements that heat and degas the fluid, either before or after it is filtered with the two or more filters 106 (e.g., polysulfone filters like dialyzers or DIASAFE Plus® filters). In some embodiments, the fluid generating system 100 includes its own system for creating reverse osmosis (purified) water before combining it with the solutes in the mixing chamber 212.

All the controllers 210 and the sensors 214 are in communication with, and receive instructions from, the control unit 202. The control unit 202 automatically instructs the controllers 210 to open/close or otherwise react in response to the fluid generation profile 208 selected by a user. For example, when a fluid generation profile 208 is loaded into the processor 204 that requires volumetric measurement, the control unit 202 instructs fluid controller 210A to operate, while keeping fluid controller 210B and 210C closed. In this example, the customized medical fluid 114 to be generated by the selected fluid generation profile 208 does not include the liquid contained in liquid solute source 110B, and does not require a solid solute. The control unit 202 detects if the solution is to be prepared using volumetric, gravimetric, or conductivity-based measurements. The control unit 202 determines if the correct liquid solute sources 110 or solid solute sources 112 for a selected fluid generation profiles 208 are attached to the machine, for example by scanning barcodes attached to liquid solute sources 110 or solid solute sources 112. If the incorrect sources are attached, or if insufficient quantities remain in the liquid solute sources 110 or solid solute sources 112, the user interface 116 may display a warning message.

The sensors 214 measure the customized medical fluid 114 once it has been prepared in the mixing chamber 212. The control unit memory 206 includes a range of acceptable values for each parameter measured by one of the sensors 214. For example, a variance of plus or minus 1% volume can be deemed to be acceptable. Once the customized medical fluid has been prepared in the mixing chamber, the sensors 214 determine if the fluid is of acceptable quality, e.g., if each fluid parameter is within the acceptable values. If one or more of the parameters is outside an acceptable range, the fluid generating system 100 may generate an error message to the user. The error message may include a visual and/or auditory signal. The fluid generating system 100 can then direct the generated fluid that has failed the quality control test to a drain and not to a reusable fluid container 104. If the all parameters are within the acceptable range, the fluid generating system 100 delivers the customized medical fluid 114 to a waiting reusable fluid container 104.

Two liquid solute sources 110A and 110B and one solid solute source 112 are illustrated in FIG. 3, but more or fewer sources of each type are possible. For example, the fluid generating system 100 can be configured to use only liquid solute sources or only solid solute sources.

In another implementation, the fluid generating system 100 can use special additive cartridges or packets in solid or liquid form to create a customized medical fluid 114. A fluid generating system 100 that uses special additive cartridges is particularly advantageous to generate 'micro-brews' of designer solutions such as may be used in a laboratory environment. Such a fluid generating system 100 may have a custom fluid generation profile 208, one that automatically empties the entire contents of an attached cartridge to use its entire contents. In some embodiments, such a fluid generating system may be a simplified system that is configured to only receive ingredients from a single source (e.g., from the special cartridge).

In another implementation, a fluid generating system that only generates a single type of medical fluid would also be particularly advantageous for mass production, e.g., within a clinic where sodium bicarbonate cartridges would be used to generate pure saline solution. For hemodialysis treatments, dialysate that has been filtered at 10-6 CFU/ml and 0.5 EU/ml is a suitable substitution for saline and could be generated by a fluid generating system 100. Such a machine would produce quality saline on-site and could be configured to fill multiple reusable bags at a time, as in FIG. 2C.

Any treatment or need for on-demand saline or other medical/laboratory fluids could be achieved with different settings stored in the memory 206 of the fluid generating system 100. For example, such customized medical fluids 114 could include normal saline (0.9% NaCl); hypotonic saline (0.45% NaCl); gelofusine: succinylated (modified fluid) gelatin and sodium chloride; oxygen carrying fluids like perfluorocarbons, carbon-fluorine emulsions, and hyperbranched polymer-protected porphyrins; lactated Ringer's solution containing 28 mmol/L lactate, 4 mmol/L K+ and 1.5 mmol/L Ca2+; Hartmann's solution or compound sodium lactate (CSL) or other crystalloid solution that is closely isotonic with blood and intended for intravenous administration; 5% dextrose (in water); 5% dextrose (in normal saline); parenteral nutrition fluids containing salts, glucose, amino acids, lipids and added vitamins. Combinations of the above fluids can also be generated, as can be any fluid that can be made from a combination of the available constituents for these fluids.

Figure 4:
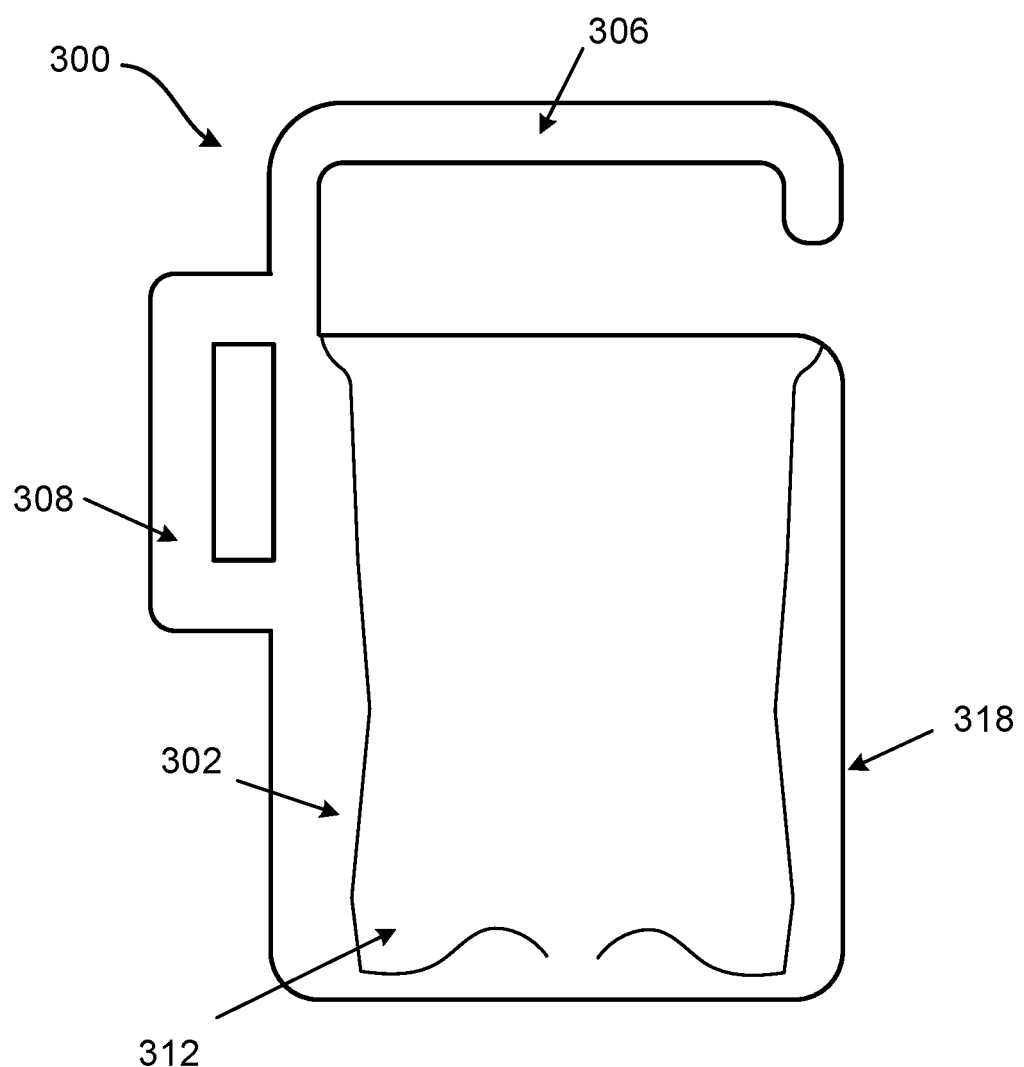
FIG. 4 is schematic of a portion of a reusable bag for use with the medical fluid generating machine of FIG. 1.
Figure 5A:
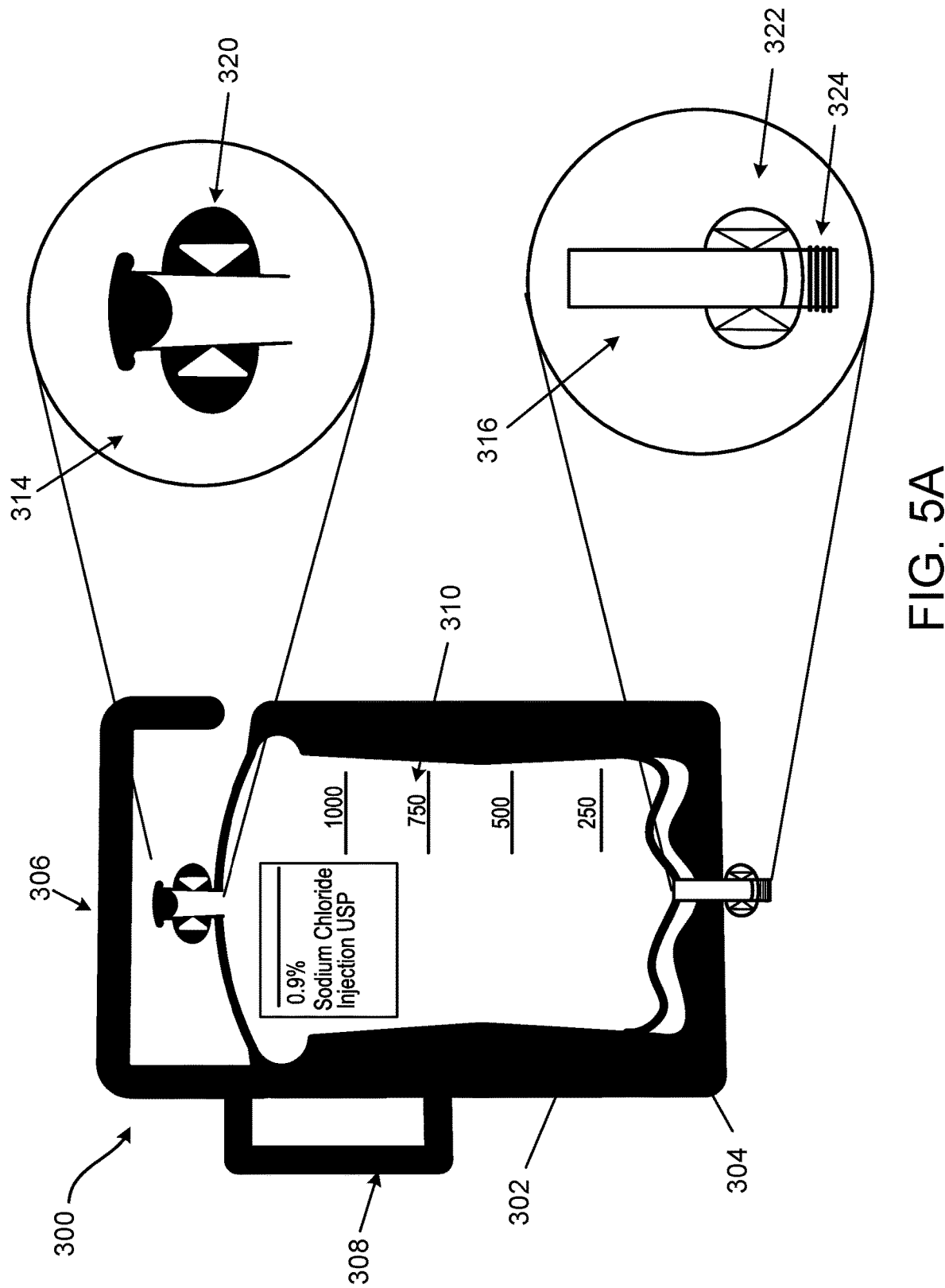
FIGS. 5A and 5B are embodiments of a reusable bag for use with the medical fluid generating machine of FIG. 1.

FIGS. 4 and 5A show an example of a reusable fluid container 300 that is suitable for use and reuse with the fluid generating system 100. The reusable fluid container 300 has two primary components, a rigid skeletal structure or exterior shell 302 that is attached to an interior disposable bag 304.

The exterior shell 302 provides strength to the reusable fluid container 300 and is made of materials that are durable and reusable, e.g., materials that are strong, fracture-resistant, and sterilizable. In some instances, the rigid shell 302 can be made with recyclable materials. In some instances, the rigid shell 302 can be sent back to the manufacturer for recycling and become eligible for recycling incentives. The exterior shell 302 has a top handle 306 to allow the reusable fluid container 300 to hang, e.g., from an IV pole. The exterior shell 306 has a handle 308 on one side, which allows a user to easily grasp and hold the reusable fluid container 300. The exterior shell 306 also includes engagement features 318, which are pins or slots to secure and fasten the reusable fluid container 300 to the fluid generation machine 102. The engagement features can be at the back, front, or sides of the exterior shell 302, and allow a user to position the reusable fluid container 300 at the container attachment site 118 in a single configuration only. The body of the rigid shell, the top handle 306, side handle 308 and the engagement features 318 can be monolithic, e.g., made from a single piece such as a single piece of extruded or injection molded plastic.

The interior disposable bag 304 is made of a flexible material that is capable of being sterilized. The interior disposable bag 304 is typically disposed of after a single use, whereas the exterior shell 306 is reusable for multiple uses (the number of uses depending on the specific material uses and relevant regulations). The disposable bag 304 is malleable and balloons when it is filled with fluid, and for convenience has volume markings 310 on a side of the disposable bag 304.

The exterior shell 302 has a shaped hollow interior 312 to which the disposable bag 304 firmly attaches, e.g., by vacuum seal or adhesive. The shaped hollow interior 312 is coated with Teflon to ensure no biological growth sticks to the walls, corners, entry-exit points that access either the fluid generation machine 102 or the patient/user.

The reusable fluid container 300 has two openings: a top opening 314 for filling the reusable fluid container 300 and for introducing disinfection fluid, and a bottom opening 316 for flushing disinfection fluid and for connecting to the patient or to something else. Fluid generally flows through the reusable fluid container 300 from the top opening 314 to the bottom opening 316, in a single direction.

The top opening 314 has a clamp 320 on top and a clamp 322 is at the bottom opening 316 to ensure there are no leaks and fluid is protected from contamination. Both clamps 320, 322 are compression clamps that can be easily opened or stoppered by a compressive force from the fluid generating system 100, permitting the machine to toggle between open and closed configurations. The bottom opening 316 pierces both the exterior shell 302 and disposable bag 304 and also has a locking mechanism 324 to ensure fluid connections are made in a secure and easy manner without compromising the sterility of the fluid within the container. The locking mechanism 324 is advantageously a self-locking luer connection. The top opening 314 and bottom opening 316 can be color-coded, for example marked by black for the top and red for the patient connection or bottom opening.

Figure 5B:
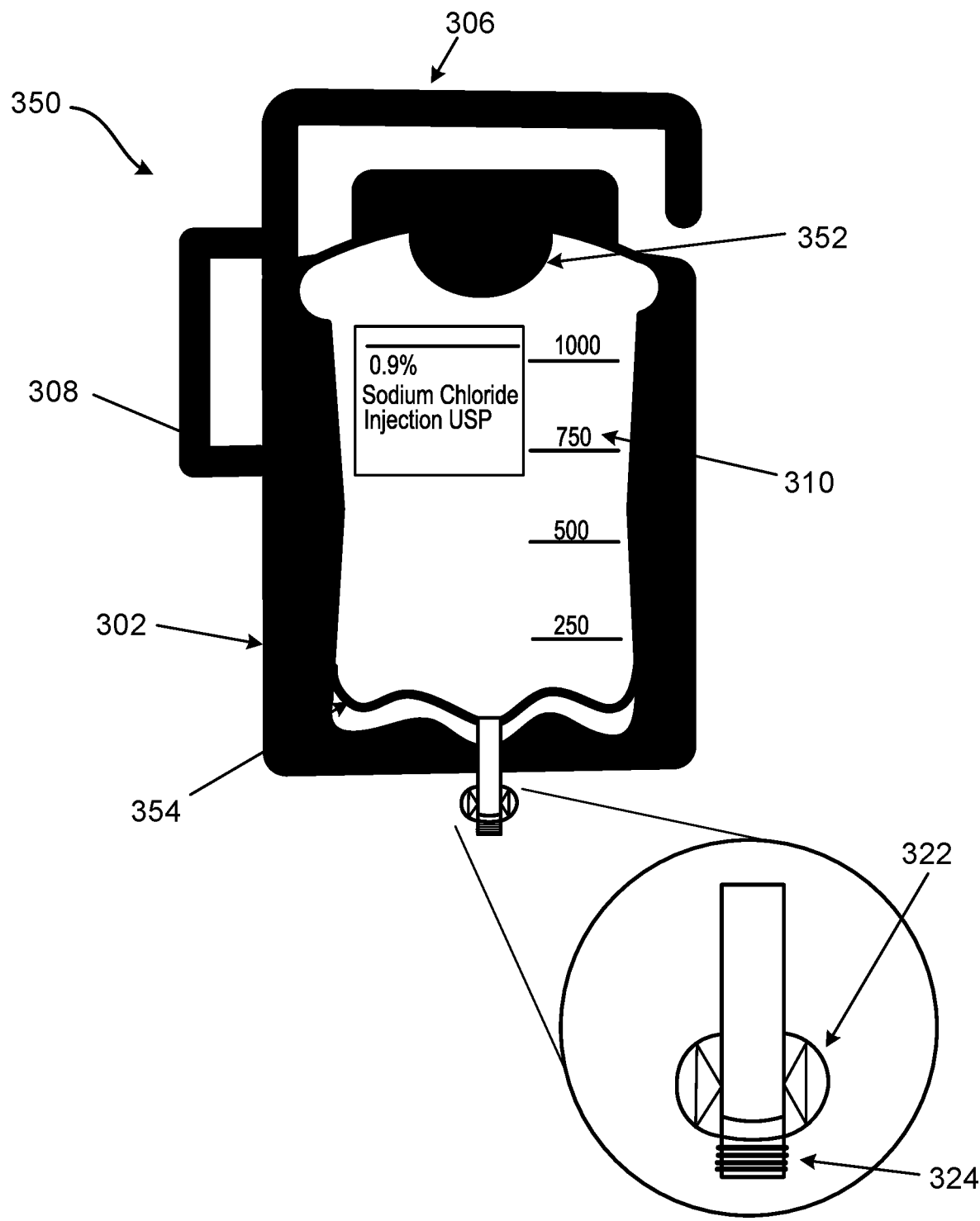

The reusable fluid container 300 shown in FIG. 5A has a narrow top opening, for maximum sterility. FIG. 5B shows a second embodiment of a reusable fluid container 350 with a wide top opening 352 of a disposable bag 354. The wide top opening is suitable for home use where a wider filling orifice may aid avoiding spills during transfer. The reusable fluid container 350 has a mechanism to seal and uphold the sterility of fluid in the pouch, by the fluid generating system 100 hermetically sealing the top end of the disposable bag 304. For example, the rigid shell can include an access feature that allows access for a heater wand to heat seal the disposable bag 354. When a user removes the reusable fluid container 300, 350 from the fluid generation machine 102, the disposable bag 354 is sealed. For use, the user accesses the fluid in the disposable bag 304, 354 from the bottom opening 316 to attach to the patient.

The reusable fluid containers 300, 350 can withstand temperatures from −20 to 50 degrees Celsius and be made of materials that can withstand a bleach or chemical disinfection required for safe use. These reusable fluid containers 300, 350 can be made to contain varying volumes, between from about 100 cc to about 6000 cc.

The user is able to disinfect the patient entry points to always ensure a sterile connection if the filled container is attached to a patient after storage. Sterility can be ensured by a properly enclosed container attachment site 118 in the fluid generation machine 102 or by soaking the container in a disinfectant bath.

The reusable fluid containers 300, 350 are suited for filling at medical fluid generating machine stations, which can be located at homes, clinics, pharmacies, hospitals, medical camps, disaster units, military units, or any healthcare facility.

Figure 6:
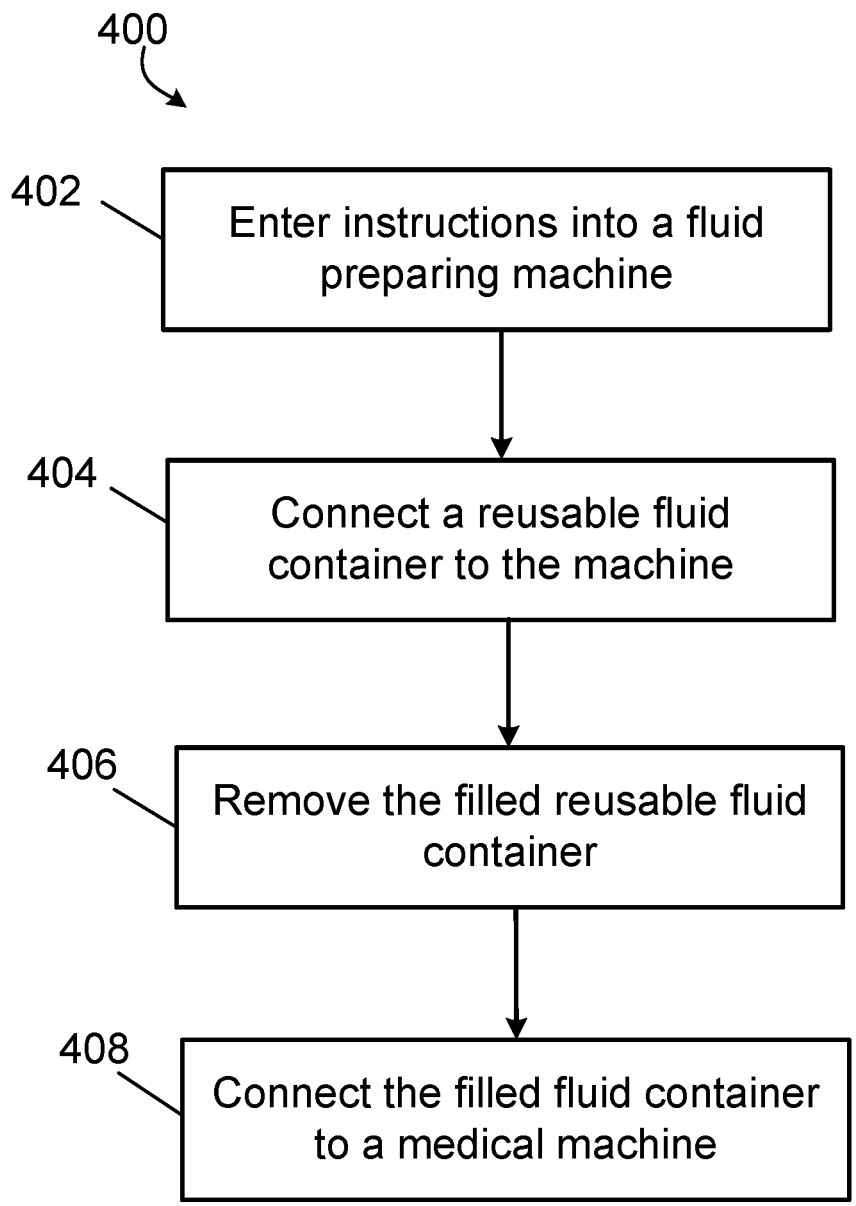
FIG. 6 is a flowchart of a method of using the medical fluid generating machine of FIG. 1.

Referring to FIG. 6, to operate the fluid generating system 100, a user may implement method 400. The user adds the raw material by connecting containers to the machine having contents in liquid or solid form to supply liquid solute sources 110 and/or solid solute sources 112 to the fluid generating system 100. At step 402, the user enters instructions into the fluid generating system 100. The user enters (e.g., selects) the desired customized medical fluid 114 at the user interface 116. The user enters (e.g., selects) the volume of fluid to be made. The volume of fluid to be generated can vary, in some cases, between a minimum of 21 mL to maximum of 101 mL. The user connects a reusable fluid container 300, 350 to the machine, step 406. The user is alerted at the user interface 116 that the fluid making is in progress, and may include additional information such as estimated time the fluid will be ready, or a progress bar. For example, the fluid generation machine 102 can make saline within 10-15 minutes and display that information on the user interface 116. The user inserts the reusable fluid container 104 (e.g., reusable fluid container 300, 350) into the filling station per the instructions that may be displayed on the user interface 116. The customized medical fluid 114 is generated and is tested through the quality checks (conductivity, etc.) to ensure its adherence to a standard formulation. The user gets a notification that the fluid is finished, typically at the user interface 116. The completed and sealed container is marked with the size of the batch and the expiry, e.g., the time by which the just-generated fluid will have to be recycled/thrown out for a fresh batch. For example, expiration label can read "Must be used before XX:XX (AM/PM) on date". The user then removes the filled reusable fluid container, step 406. The container is ready for the user to connect the filled fluid container to a medical machine, step 408. In some instances, when the reusable fluid container 104 is expired it displays a red color to indicate expiration (e.g., on an LCD screen).

In some embodiments, the machine can refill between two and eight reusable fluid containers 104 in parallel. Sensors on the fluid generation machine 102 can determine when a bag to be filled has been inserted and when it should be removed from the machine, preventing any spills or cross-contamination. The fluid generating system 100 can keep a count of fluid units made and send metrics to a remote source, e.g., an inventory tracking system. The fluid generating system 100 can thus alert the user it may be desirable to fill empty reusable fluid containers 104 if insufficient volume of a fluid is in storage in the inventory.

The hydraulic system 200 is frequently disinfected, e.g., between different kinds of infusates (if different fluid types are chosen at a machine site), automatically at the end of a day, or at a user-chosen time. A residual disinfectant check can be part of the hydraulic disinfection. The reusable fluid containers 104 can also be disinfected both inside and outside, rinsed and tested for perforations, biologics, and residual disinfectant after or before each use.

The fluid generating system 100 can automatically be turned on to make a fluid (e.g., saline) at a programmed time or times every day or every week.

To ensure sterility, the container attachment site 118 of the fluid generation machine 102 may be enclosed within the body of the fluid generation machine 102. The fluid generation machine 102 can include a button or touch-operated mechanism to open/close a door so that the user can insert/remove the reusable fluid container 104 to or from a receiving cavity within and register the engagement features 318 to secure it within. Without interference from the user, the fluid generating system 100 will be able to disinfect the top opening 316 and seal the top opening 316 once the container is filled.

Figure 7:
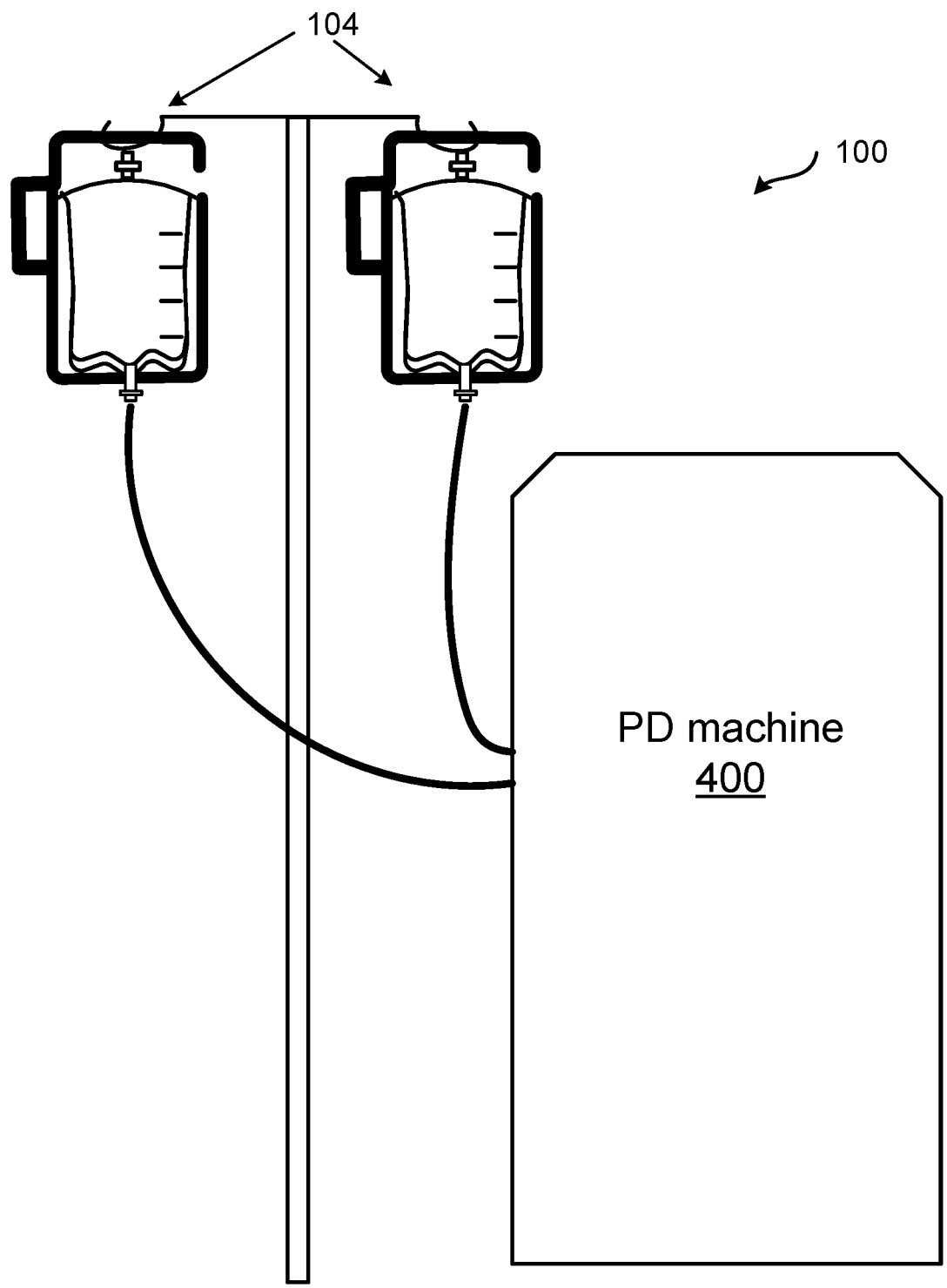
FIG. 7 is schematic of a therapeutic system using a reusable bag filled by the medical fluid generating machine of FIG. 1.

A simple workflow in which the reusable fluid container 104 is used in a clinic can include the reusable fluid container 104 being received in packaging by a user. The user opens the package to inspect the reusable fluid container 104. Once attached, the fluid generation machine 102 disinfects the reusable fluid container 104, and fills the reusable fluid container 104 with saline or any fluid for medical use. The fluid label 126 in some instances can include a specific patient ID label for the customized medical fluid to be delivered to a particular patient. The fluid label 126 has a code that includes a batch number, timestamp of preparation, and time stamp for expiration. Referring to FIG. 7, the filled reusable fluid container 104 (or multiple containers) is now moved to the patient location, e.g., a therapeutic machine 400 such as a PD system that uses gravity. The patient is connected to the reusable fluid containers 104 either directly or indirectly via the therapeutic machine 400. Once treatment is complete or the reusable fluid container 104 is emptied, whichever happens first, the reusable fluid container 104 is removed. The reusable fluid container 104 can be disinfected using the fluid generating system 100 and stored in a sterile location.

Figure 8:
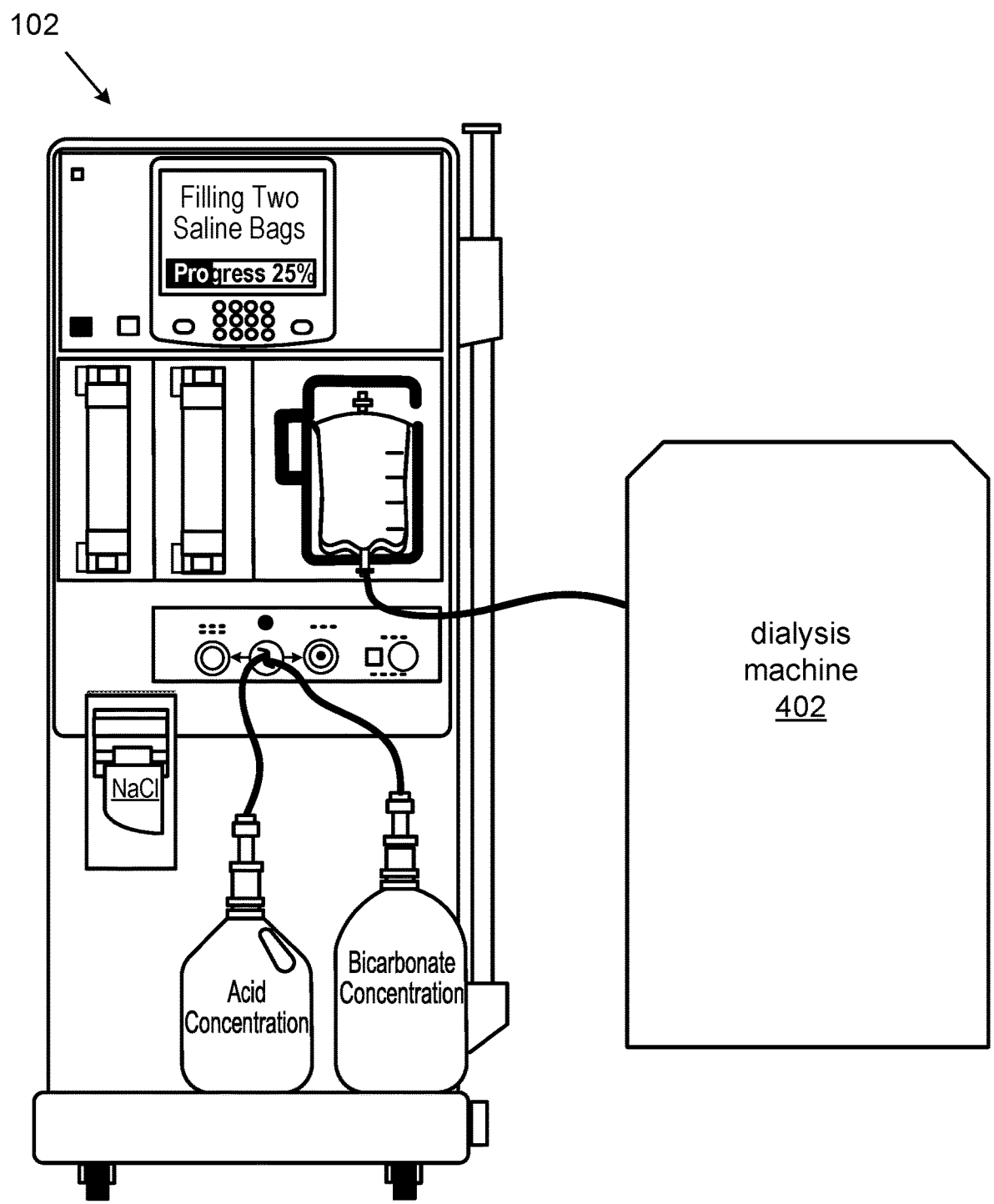
FIG. 8 is schematic of a therapeutic system directly using a reusable bag filled by the medical fluid generating machine of FIG. 1.

The fluid generating system 100 need not fill reusable fluid containers, but could instead fill single-use containers. Referring to FIG. 8 the fluid generation machine 102 is directly fluidly attachable to a dialysis machine 402. In this configuration, the fluid generation machine 102 acts to make fluid online, rather than input into bags. For example, the therapeutic machine 402 can be a peritoneal dialysis machine, or machine for hemodialysis, hemofiltration, hemodiafiltration, cardiopulmonary machine, apheresis machine, etc.

A number of embodiments of the invention have been described. Nevertheless, it will be understood that various modifications may be made without departing from the spirit and scope of the invention. Accordingly, other embodiments are within the scope of the following claims.

What is claimed is:

1. A method of preparing dialysate or saline or hypotonic saline with a medical fluid generating machine, the method comprising:
   receiving, at the medical fluid generating machine, a container to be filled with the dialysate or saline or hypotonic saline;
   receiving, at a processor, instructions to prepare the dialysate or saline or hypotonic saline, the instructions including an identification of a medical fluid type from among dialysate or saline or hypotonic saline and a desired volume of the dialysate or saline or hypotonic saline;
   preparing the dialysate or saline or hypotonic saline according to the received instructions;
   testing the prepared dialysate or saline or hypotonic saline to ensure that one or more characteristics of the prepared dialysate or saline or hypotonic saline is within an acceptable range;
   filling the container with the prepared dialysate or saline or hypotonic saline; and
   labelling the container with information about the dialysate or saline or hypotonic saline, the information including the identification of the medical fluid type within the filled container, and an expiration date of the dialysate or saline or hypotonic saline.

2. The method of claim 1, wherein preparing the dialysate or saline or hypotonic saline comprises automatically determining if the dialysate or saline or hypotonic saline is to be measured using gravimetric, volumetric, or conductivity-based measurements.

3. The method of claim 1, wherein preparing the dialysate or saline or hypotonic saline comprises selecting one or more solutes from a plurality of available solute sources to prepare the dialysate or saline or hypotonic saline based on the identified medical fluid type, measuring a required amount of the one or more solutes based on the desired volume, delivering the measured amounts of the one or more solutes to a reservoir within the machine, and mixing the delivered amounts of one or more solutes with a volume of water, the volume of water determined by the desired volume.

4. The method of claim 3, wherein preparing the dialysate or saline or hypotonic saline comprises selecting one or more solutes from a plurality of solute sources to prepare the dialysate or saline or hypotonic saline based on the identification of the medical fluid type and displaying an alert if one or more of the selected solute sources is not available to the machine.

5. The method of claim 1, comprising displaying an alert that the prepared dialysate or saline or hypotonic saline is defective upon detecting that the one or more characteristics of the prepared dialysate or saline or hypotonic saline is not within the acceptable range.

6. The method of claim 1, comprising sterilizing the container prior to filling the container with fluid.

7. The method of claim 6, wherein sterilizing the container comprises filling the container with disinfectant and emptying the disinfectant from the container.

8. The method of claim 6, wherein sterilizing comprises irradiating the container with UV radiation.

9. The method of claim 1, wherein labelling the container comprises affixing a label to an outside of the container.

10. The method of claim 1, wherein labelling the container comprises sending instructions to a screen affixed to the container to display the information about the dialysate or saline or hypotonic saline.

11. The method of claim 1, comprising sealing a side of the filled container to maintain sterility of the dialysate or saline or hypotonic saline within the filled container.

12. The method of claim 11, wherein sealing a side of the filled container comprises hermetically sealing a flexible bag of the container which is affixed within a rigid shell of the container.

13. The method of claim 12, wherein the flexible bag is releasably secured to the rigid shell.

14. The method of claim 1, wherein the identified medical fluid type is saline.

15. The method of claim 1, wherein the identified medical fluid type is dialysate.

16. The method of claim 1, wherein the machine includes a door that opens to uncover a cavity that receives the container.

17. The method of claim 1, wherein the machine is configured for connecting different concentrates to the machine and allowing a user to select any one of dialysate or saline or hypotonic saline.

18. A method comprising:
receiving, at a medical fluid generating machine, a container to be filled with a saline substitute;
receiving, at a processor, instructions to prepare the saline substitute;
preparing the saline substitute in response to the instructions by (a) combining water with an acid concentration and a bicarbonate concentration to form a solution and (b) filtering the solution through one or more filters to achieve a purity of no more than $10^{-6}$ CFU/ml and no more than 0.5 EU/ml;
testing the prepared saline substitute to ensure that one or more characteristics of the prepared saline substitute is within an acceptable range;
filling the container with the tested saline substitute; and
labelling the container with information that identifies the saline substitute and provides an expiration date of the saline substitute.

19. The method of claim 18, wherein preparing the saline substitute further comprises heating and degassing the solution.

20. The method of claim 18, further comprising priming a dialysis machine by flowing the prepared saline substitute into a blood line of the dialysis machine prior to a dialysis treatment.

21. The method of claim 20, further comprising performing the dialysis treatment on a patient.

22. The method of claim 21, further comprising flushing blood from the blood line back to the patient by pushing the prepared saline substitute into the blood line.

* * * * *